(12) United States Patent
Dziura

(10) Patent No.: US 8,090,558 B1
(45) Date of Patent: Jan. 3, 2012

(54) OPTICAL PARAMETRIC MODEL OPTIMIZATION

(75) Inventor: Thaddeus G. Dziura, San Jose, CA (US)

(73) Assignee: KLA-Tencor Corporation, Milpitas, CA (US)

(*) Notice: Subject to any disclaimer, the term of this patent is extended or adjusted under 35 U.S.C. 154(b) by 351 days.

(21) Appl. No.: 12/477,459

(22) Filed: Jun. 3, 2009

Related U.S. Application Data

(60) Provisional application No. 61/059,911, filed on Jun. 9, 2008.

(51) Int. Cl.
- G06F 7/60 (2006.01)
- G06F 3/00 (2006.01)
- G06G 7/48 (2006.01)
- G01J 3/40 (2006.01)
- G01J 3/42 (2006.01)
- G06E 3/00 (2006.01)
- G01R 27/28 (2006.01)
- G01B 5/02 (2006.01)

(52) U.S. Cl. ........... 703/2; 356/302; 356/303; 356/319; 356/451; 359/107; 359/108; 702/117; 702/159; 702/172; 703/3; 703/4; 703/5; 703/13

(58) Field of Classification Search .......... 356/302, 356/303, 319, 451; 359/107, 108; 702/117, 702/159, 172; 703/2, 3, 4, 5, 13
See application file for complete search history.

(56) References Cited

U.S. PATENT DOCUMENTS

| | | | |
|---|---|---|---|
| 5,308,982 A * | 5/1994 | Ivaldi et al. | 250/339.12 |
| 5,607,800 A | 3/1997 | Ziger | |
| 5,963,329 A | 10/1999 | Conrad et al. | |
| 6,137,104 A * | 10/2000 | Webb et al. | 250/226 |
| 6,483,580 B1 | 11/2002 | Xu et al. | |
| 6,687,630 B2 * | 2/2004 | Dionne | 702/76 |
| 6,900,892 B2 | 5/2005 | Shchegrov et al. | |
| 7,072,049 B2 | 7/2006 | Niu et al. | |
| 7,092,110 B2 | 8/2006 | Balasubramanian et al. | |
| 7,126,700 B2 | 10/2006 | Bao et al. | |
| 7,127,372 B2 * | 10/2006 | Boysworth | 702/179 |
| 7,171,284 B2 | 1/2007 | Vuong et al. | |
| 7,399,975 B2 * | 7/2008 | Harrison | 250/372 |
| 7,400,398 B2 * | 7/2008 | Stedman | 356/326 |
| 7,505,153 B2 | 3/2009 | Vuong et al. | |
| 2003/0219797 A1 * | 11/2003 | Zhao et al. | 435/6 |
| 2007/0179753 A1 * | 8/2007 | Barajas et al. | 702/189 |
| 2008/0021681 A1 * | 1/2008 | Grichnik et al. | 703/2 |

OTHER PUBLICATIONS

Podraza et al. "Analysis of the optical properties and structure of sculptured thin films from spectroscopic Mueller matrix ellipsometry", Thin Solid Films 455-456 (2004) 571-575.*

(Continued)

*Primary Examiner* — Kamini S Shah
*Assistant Examiner* — Shambhavi Patel
(74) *Attorney, Agent, or Firm* — Luedeka, Neely & Graham, P.C.

(57) ABSTRACT

A method is presented for selecting the order in which parameters are evaluated for inclusion in a model of a film stack, which is by ranking them according to measurement precision. Further, a method is presented for determining which parameters are to be floated, set, or discarded from the model, which is by determining whether average chi-square and chi-square uniformity decreases or increases when the parameter is added to the model. In this manner, a model for the film stack can be quickly assembles with a high degree of accuracy.

1 Claim, 2 Drawing Sheets

OTHER PUBLICATIONS

Tallon-Bose et al. "Model Fitting Tutorial", May 2007.*
Bosch et al. "Optical characterization of materials deposited by different processes: the LaF3 in the UV-visible region", 2000.*
Leinfellner et al. "A software for optical characterization of thin Films for microelectronic applications", Microelectronics Reliability 40 (2000) 873-875.*
Blayo et al, "Ultraviolet-visible ellipsometry for process control during etching of submicrometer features", J. Opt. Soc. Am. A, 12, 591-599 (1995).

Mills et al. "Spectral ellipsometry on patterned wafers", Proceedings of SPIE Conference on Process, Equipment, and Material Control in Integrated Circuit Manufacturing, Sabnis & Raaijmakers, eds., 2637, 194-203, (Oct. 25-26, 1995).

Arimoto, "Precise Line-and-Space Monitoring Results by Ellipsometry", Japn., J. Appl. Phys. 36, 173-175 (1997).

* cited by examiner

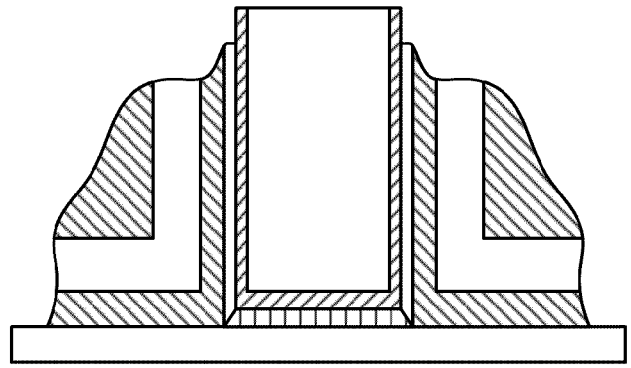

Fig. 1

Parameter Name

SubstratePeriod
G3MiddleCD
G3HT
G3WA
G3Bow
G1HT
G1WA
G2HT
G2WA
G3TopRound
S1DeltaHT
S1Width
S1Thickness
S1Gamma
S1HorizontalSlope
S1VerticalSlope
S2DeltaHT
S2Width
S2Thickness S2Gamma
S2HorizontalSlope
S2VerticalSlope
S3DeltaHT
S3Width
S3Thickness
S3Gamma
S3HorizontalSlope
S3VerticalSlope
S4DeltaHT
S4DeltaWidth
S4Thickness
S4Gamma
S4HorizontalSlope
S4VerticalSlope
S5DeltaHT
S5DeltaWidth
S5WA
S5VerticalSlope

Fig. 2

OPTICAL PARAMETRIC MODEL OPTIMIZATION

This application claims all rights on and priority to U.S. provisional application Ser. No. 61/059,911 filed 2008, Jun. 9, the entirety of the disclosure of which is included herein by reference. This invention relates to the field of measurement tools for the integrated circuit fabrication industry. More particularly, this invention relates to optical measurement of complex film stacks, such as those formed during integrated circuit fabrication processes.

BACKGROUND

Field

During integrated circuit fabrication processes, the integrated circuits typically receive a variety of optical measurements. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

These optical measurements include measurements such as the thickness of complex stacks of thin films on a substrate, and critical dimensions of the structures that are formed on the substrate. As used herein, the term "substrate" refers to the substrates on which the integrated circuits are fabricated, the masks or reticles from which the patterns used to form the integrated circuits are transferred, and other types of substrates as used in the integrated circuit fabrication industry. As used herein, "film stack" also refers to a device-like structure, typically formed in a spatially periodic diffraction grating-like metrology target, containing multiple film materials, from which optical measurements extract information on critical dimension.

These measurements are generally made by directing a beam of light onto the surface of the substrate, and then comparing the properties of the light reflected back from the substrate against the properties of the incident beam. These measured properties of the lights are fed into a complex mathematical model of the film stack, where the various metrics, such as film thickness of the different layers, are iteratively adjusted, until an error measurement in the underlying equations is reduced below a desired degree of accuracy. The assumed thicknesses that produced the degree of accuracy are then reported as the thicknesses of the various layers.

The mathematical models of the film stacks can be extremely complicated both to construct and to solve. One reason for this is the large number of film stack properties that could be included in the model. If all of the properties where included in the model, the model would be extremely precise, but would require an inordinate amount of time to compute. Including just one property in the model would require relatively little calculation time, but would tend to be extremely inaccurate. Thus, determining which properties to include and how many properties to include in the development of the mathematical model by which the film stack characteristics are calculated is an important task.

Traditionally, an applications engineer makes a list of all the parameters describing the film stack (film thickness, critical dimension, overlay), and through experience with previously-developed models for similar films, or through intuition about how signal to noise ratio scales with physical size, selects the parameters to include (also called float) in the model. Final model optimization was then performed through trial and error.

This method is extremely slow, as several candidate models typically need to be tested and compared. For models with moderate dimensionality (number of parameters), the optimization process can take from a few days to a week. For models with high dimensionality, the process can take several weeks. Further, optical metrology tools in particular are required to provide good measurement performance on structures having as many as twenty to forty degrees of freedom (number of parameters). It is impossible for the applications engineer to consistently and systematically rank the importance of such a large number of parameters. This means that different engineers deliver different measurement recipes for the same dataset.

What is needed, therefore, is a method for determining the properties of a film stack to include in a mathematical model of the film stack, so that the model provides a sufficiently accurate representation of the film stack, without requiring an inordinate amount of time to calculate.

SUMMARY

The above and other needs are met by a computerized method of constructing a mathematical model of a film stack having parameters, using the steps of:

a. estimating a measurement precision value for each parameter,
b. normalizing each measurement precision value,
c. ordering the normalized precision values from lowest to highest,
d. collecting spectral data from the film stack at multiple locations,
e. constructing with a processor a model with a subset of the parameters having the lowest normalized precision values,
f. fitting the model to the spectral data,
g. computing with the processor average chi-square and chi-square nonuniformity three-sigma metrics for the model,
h. selecting a next parameter with a lowest normalized precision values,
i. adding the next parameter to the existing model to create a modified model,
j. fitting the modified model to the spectral data,
k. computing with the processor average chi-square and chi-square nonuniformity three-sigma metrics for the modified model,
l. comparing the average chi-square and chi-square nonuniformity for the modified model and the existing model,
m. when the average chi-square and chi-square nonuniformity are both reduced in the modified model, then retaining the next parameter in the modified model as a floated parameter, and designating the modified model as the existing model,
n. when the average chi-square is reduced and the chi-square nonuniformity increases in the modified model, then including the next parameter in the modified model as a constant that is set to a value that is an average of the parameters spectral data, and designating the modified model as the existing model,
o. when average chi-square is not reduced in the modified model, then discarding the modified model, and p. iteratively repeating steps i-o with the processor until either all of the parameters have been investigated or a desired number of parameters have been added to the modified model.

In this manner, a method is presented for selecting the order in which parameters are evaluated for inclusion in the model, which is by ranking them according to measurement precision. Further, a method is presented for determining which parameters are to be floated, set, or discarded from the model, which is by determining whether average chi-square and chi-square uniformity decreases or increases when the parameter is added to the model. In this manner, a model for the film stack can be quickly assembled with a high degree of accuracy.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIG. 1 is a cross section depiction of a spacer for an integrated circuit.

FIG. 2 is a list of various parameters for the spacer of FIG. 1.

DETAILED DESCRIPTION

Figure 3:
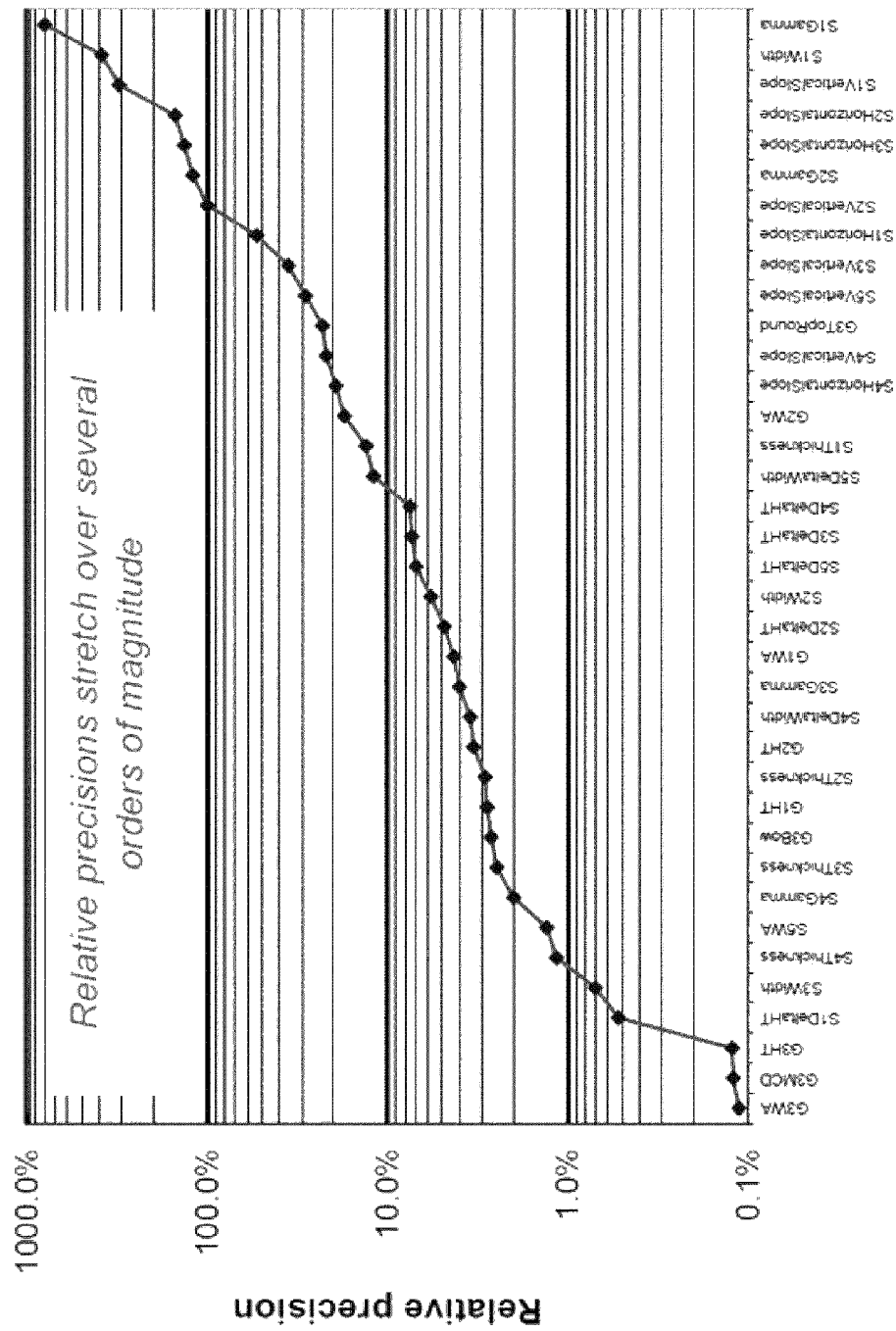
FIG. 3 is a graph depicting the relative precisions of the various parameters listed in FIG. 2.

One benefit of the various embodiments according to the present invention is a systematic and automatable method for selecting parameters to float in an optical parametric model, through the use of certain metrics, to provide a good model fit to the data. The method consists of three basic steps, as described in the sections below.

Single Parameter Precision Estimation

In this step, a set of sub models is constructed, in which for each sub model a single parameter is floated (one degree of freedom). Using standard techniques the measurement precision is estimated and reported as a three-sigma value, for each individual model parameter. Correlation between pairs of model parameters is not a factor because only one parameter at a time is floated.

For example, the parameter list for a given structure, such as a spacer as depicted in FIG. 1, could include 37 different parameters, such as: G3WA, G3MCD, G3HT, S1DeltaHT, S3Width, S4Thickness, S5WA, S4Gamma, S3Thickness, G3Bow, G1HT, S2Thickness, G2HT, S4DeltaWidth, S3Gamma, G1WA, S2DeltaHT, S2Width, S5DeltaHT, S3DeltaHT, S4DeltaHT, S5DeltaWidth, S1Thickness, G2WA, S4HorizontalSlope, S4VerticalSlope, G3TopRound, S5VerticalSlope, S3VerticalSlope, S1HorizontalSlope, S2VerticalSlope, S2Gamma, S3HorizontalSlope, S2HorizontalSlope, S1VerticalSlope, S1Width, and S1Gamma.

Precision Normalization and Parameter Ranking

The three-sigma precision obtained above in step one is normalized by the nominal value of each corresponding model parameter, thereby representing the precision as a relative value. These relative precision values are then sorted from lowest to highest (parameters with smaller relative precision are more important). An example of such a ranking is provide in FIG. 3 for the parameters introduced above for the spacer of FIG. 1.

Final Parameter Selection and Model Optimization

Spectral data is collected at several sites across the substrate. First, a model with a low number of degrees of freedom is constructed (such as three degrees of freedom). The parameters in the model are the topmost sensitive ones from step two above, or in other words, the parameters having the smaller relative precision values. The model is then fit to the spectral data at all locations on the substrate. The average chi-square and chi-square nonuniformity three-sigma metrics are then computed.

The methods by which the models are constructing are known in the industry, and can vary by application. However, this process determines which parameters to try to fit into the model (as determined in step two), and then whether the parameter will remain in the model, as determined in this step three.

The next most important model parameter is then added to the model as an additional degree of freedom, and the new model is fit to the spectral data. Average chi-square and chi-square nonuniformity are then compared between this model and the previous model. If average chi-square and chi-square nonuniformity are both reduced, the new parameter is retained in the model as a floated parameter. If average chi-square decreases, but chi-square nonuniformity increases, the parameter is not retained in the model as a floated parameter, but is included within the model as a constant, and set to the value that is obtained from the average measurements on the substrates. If average chi-square does not decrease, the parameter is not added as a floated parameter, and its nominal value is not corrected.

The process is iterated, by adding one parameter at a time as a possible candidate parameter, in decreasing order of parameter importance (as determined in step two above). The process terminates either when all parameters have been considered for inclusion in the model, or some suitable maximum number of degrees of freedom in the model is reached.

The method as described above has already been demonstrated to optimize six degree of freedom models in two to three hours, and ten degree of freedom models in approximately two days. The method is applicable to model-based metrology for films, critical dimension, and overlay.

As an alternate, any other sensitivity-based method of parameter ranking may be used, for example—principal component analysis. The sensitivity may be normalized to other metrics, for example real or anticipated cross-substrate uniformity. Some goodness-of-fit metric other than chi-square may be used, such as root-mean-square error.

The method can be automated in a desktop-based optical data analysis software. The user would enter nominal values for a film stack, optical critical dimension grating target, or overlay target. The software would then automatically determine which parameters were best to float, and optimize the nominal value of each parameter.

Thus, the methods according to the present invention provide a systematic way of choosing parameters to float in a model, with metrics for determining which and how many parameters are required to get accurate parametric results. In this manner, the time to complete the optimization process of the model for the film stack is dramatically reduced. New aspects of the methods include the step of ranking parameter importance from best relative precision to worst, and the step of comparing average chi-square and chi-square uniformity between models as a degree of freedom is added, to decide whether the parameter is retained in the model as a floated parameter.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A computerized method of constructing a mathematical model of a film stack having parameters, the method comprising the steps of:
  a. estimating a measurement precision value for each parameter,
  b. normalizing each measurement precision value,
  c. ordering the normalized precision values from lowest to highest,
  d. collecting spectral data from the film stack at multiple locations,
  e. constructing with a processor a model with a subset of the parameters having the lowest normalized precision values,
  f. fitting the model to the spectral data,
  g. computing with the processor average chi-square and chi-square nonuniformity three-sigma metrics for the model,
  h. selecting a next parameter with a lowest normalized precision values,
  i. adding the next parameter to the existing model to create a modified model,
  j. fitting the modified model to the spectral data,
  k. computing with the processor average chi-square and chi-square nonuniformity three-sigma metrics for the modified model,
  l. comparing the average chi-square and chi-square nonuniformity for the modified model and the existing model,
  m. when the average chi-square and chi-square nonuniformity are both reduced in the modified model, then retaining the next parameter in the modified model as a floated parameter, and designating the modified model as the existing model,
  n. when the average chi-square is reduced and the chi-square nonuniformity increases in the modified model, then including the next parameter in the modified model as a constant that is set to a value that is an average of the parameters spectral data, and designating the modified model as the existing model,
  o. when average chi-square is not reduced in the modified model, then discarding the modified model, and
  p. iteratively repeating steps i-o with the processor until either all of the parameters have been investigated or a desired number of parameters have been added to the modified model.

* * * * *